(12) United States Patent
Baldauf et al.

(10) Patent No.: US 7,704,901 B2
(45) Date of Patent: Apr. 27, 2010

(54) METHOD FOR PRODUCING A LAMINATE MATERIAL WEB HAVING ELASTIC AND NON-ELASTIC REGIONS

(75) Inventors: Georg Baldauf, Laer (DE); Herbert Bader, Steinfurt-Borghorst (DE); Josef Leuders, Gronau-Epe (DE); Marcus Schönbeck, Versmold (DE)

(73) Assignee: Nordenia Deutschland Gronau GmbH, Gronau (DE)

( * ) Notice: Subject to any disclaimer, the term of this patent is extended or adjusted under 35 U.S.C. 154(b) by 273 days.

(21) Appl. No.: 12/012,195

(22) Filed: Jan. 31, 2008

(65) Prior Publication Data

US 2008/0128077 A1    Jun. 5, 2008

Related U.S. Application Data

(62) Division of application No. 11/250,793, filed on Oct. 14, 2005, now Pat. No. 7,422,991.

(30) Foreign Application Priority Data

Jun. 23, 2005   (EP)   .................................. 05013588

(51) Int. Cl.
 *B32B 27/12*   (2006.01)
 *B32B 37/00*   (2006.01)
 *B29C 65/00*   (2006.01)

(52) U.S. Cl. ........................ 442/394; 156/290; 156/291; 156/292; 156/308.2; 156/321

(58) Field of Classification Search ................ 442/328, 442/329, 361, 373, 382, 394, 381; 156/275.7, 156/290–292, 308.2, 321
See application file for complete search history.

(56) References Cited

U.S. PATENT DOCUMENTS 7,083,691 B2    8/2006    Hamulski et al.

FOREIGN PATENT DOCUMENTS

DE         102 02 333         8/2003

*Primary Examiner*—Lynda Salvatore
(74) *Attorney, Agent, or Firm*—Collard & Roe, P.C.

(57) ABSTRACT

A method for producing an elastic laminate material web that has elastic and non-elastic regions and has non-woven fabric on both surfaces of the web. In between the two surfaces, there are film strips of an elastic film. One surface of the web consists of a planar non-woven fabric layer and is connected with non-woven fabric that is disposed on the opposite surface of the web in areas between the film strips. Each film strip is connected with a non-woven fabric layer to form a laminate strip. The laminate strips are glued to the planar non-woven fabric layer on their film side, and the non-woven fabric that is connected with the planar non-woven fabric layer between the laminate strips is in the form of non-woven fabric strips that run parallel to the laminate strips. The non-woven fabric strips overlap the non-woven fabric layer of the laminate strips in edge regions of the laminate strips.

10 Claims, 4 Drawing Sheets

METHOD FOR PRODUCING A LAMINATE MATERIAL WEB HAVING ELASTIC AND NON-ELASTIC REGIONS

CROSS-REFERENCE TO RELATED APPLICATIONS

This application is a divisional of U.S. patent application Ser. No. 11/250,793, now U.S. Pat. No. 7,422,991 filed on Oct. 14, 2005. This application also claims priority under 35 USC §119 of European Patent Application No. 05013588.8, filed on Jun. 23, 2005.

BACKGROUND OF THE INVENTION

1. Field of the Invention

The invention relates to a laminate material web having elastic and non-elastic regions, which has non-woven fabric on both surfaces. In between these surface there are sections of film strips of an elastic film. One surface is present in the form of a planar non-woven fabric layer, and the non-woven fabric layer, between the film strips, is connected with non-woven fabric that is disposed on the opposite surface of the laminate material web. The invention also relates to a method for producing the laminate material web. Sections of such a laminate material web are suitable, for example, for the production of hygiene products, on which they can be used as elastic end regions or elastic closure strips.

2. The Prior Art

A laminate material web and a method for its production is described in German Patent NO. DE 102 02 333 A1. This patent describes a procedure where thermoplastic elastomer is introduced between two non-woven fabric webs in the melted, viscous state, in the form of strips. The non-woven fabric webs are glued together over the area between the strips of the thermoplastic elastomer. The laminate material web is elastic in the region of the film strips, in the crosswise direction, and non-elastic between the film strips, where the non-woven fabric webs have been glued together over their area. With this known method, the extrusion of the thermoplastic elastomer must be coordinated with the lamination procedure, and the width of the elastic film strips is predetermined by the use of special extrusion dies. The material of the non-woven fabric webs must be selected so that high tear strength and great elasticity can be achieved.

SUMMARY OF THE INVENTION

It is therefore an object of the invention to provide a laminate material web, as well as a method for its production, which has an improved tear resistance, at greater elasticity, and is also flexible to produce.

This task is accomplished, according to the invention by providing a film strip glued to a non-woven fabric layer, to form a laminate strip. Several laminate strips are glued to a planar non-woven fabric layer on their film side. A non-woven fabric is connected with the planar non-woven fabric layer between the laminate strips. This non-woven fabric is present in the form of non-woven fabric strips that run parallel to the laminate strips and overlap the non-woven fabric layer of the laminate strips in edge regions of the laminate strips. The laminate material web according to the invention is elastic in the regions of the laminate strips, crosswise to their longitudinal direction, and non-elastic between the laminate strips. The elastic properties and the tear strength of the laminate material web can be changed, in targeted manner, both by means of the structure of the laminate strips and by means of the structure of the non-woven fabric strips.

Preferably, the non-woven fabric strips between the laminate strips are glued to the planar non-woven fabric layer over their entire area. However, the invention also comprises other methods of connection, such as a connection by means of ultrasound bonding or thermal bonding, for example.

The film strip of a laminate strip preferably consists of a mono-film of a thermoplastic elastomer. In particular, film strips of a polymer from the group of styrene-butadiene-styrene copolymers (SBS), styrene-isoprene-styrene block copolymers (SIS), styrene-ethene/butene-styrene copolymers (SEBS), elastic polyethylene copolymers, elastic polypropylene copolymers, elastic polyurethane copolymers, elastic polyamide copolymers, or a mixture of these polymers are suitable. Other polymers could also be used. In addition to the use of mono-films, co-extruded films can also be used, whereby co-extruded films having several identical layers are particularly preferred. Film strips having a thickness between 5 and 150 μm, preferably more than 10 μm and less than 130 μm, are particularly preferred.

The laminate strips consisting of an elastic film and a non-woven fabric laminated onto it are a pre-product that can be processed from a roll. The non-woven fabric of the laminate strips is glued to the elastic film. Hot-melt glues are particularly preferred. Particularly good elastic properties of the laminate material web can be achieved if the two layers of the laminate strip are connected with straight-line or wave-shaped strips of adhesive, which run along the direction of the laminate strip. In a preferred embodiment of the invention, the non-woven fabric of the laminate strips is an elastic spun-bonded fabric, but carded non-woven fabrics or non-elastic spunbonded fabrics made of polypropylene, polyethylene, polyamide, or polyethylene terephthalate can also be used. Elastic spunbonded fabrics on the basis of core/mantle multi-filaments having elastic core polymers such as elastic polypropylene copolymers or polyurethanes are particularly suitable, whereby polypropylene or polyethylene is used as the mantle polymer, for example. Aside from laminate strips in which the film strips are glued to the non-woven fabric layer, laminate strips in which the film strips are connected with the non-woven fabric layer without glue, by means of extrusion lamination or other means, can also be used within the scope of the invention. Although thermoplastic elastomers typically demonstrate great tackiness, the laminates used can be rolled onto rolls, stored, transported, and processed, as a pre-product, since the laminate is effectively prevented from sticking together by means of the non-woven fabric layer, and the tensile strength of the laminate is increased.

The planar non-woven fabric layer typically has a weight per unit area of between 5 $g/m^2$ and 50 $g/m^2$, preferably between 20 $g/m^2$ and 40 $g/m^2$. Preferably, a carded fiber non-woven fabric is used. Aside from carded fiber non-woven fabrics, spunbonded non-woven fabrics can also be used, for example, which typically have a weight per area unit between 10 $g/m^2$ and 30 $g/m^2$. The planar non-woven fabric layer consists, for example, of fibers made from polyethylene terephthalate, polyamide, polyethylene, preferably from polypropylene. Other materials could also be used.

The laminate strips are connected with the planar non-woven fabric layer by means of an adhesive, preferably a hot-melt glue, on their film side. The adhesive is preferably present in the form of straight-line or wave-shaped strips of adhesive that run along the direction of the laminate strips. Between the laminate strips, the non-woven fabric layer is connected with non-woven fabric strips. In a preferred embodiment of the invention, the adhesive is applied to the planar non-woven fabric layer at a weight per area unit between 2 g/m² and 20 g/m², preferably between 5 g/m² and 10 g/m², before the non-woven fabric layer is connected with the laminate strips and the non-woven fabric strips. Non-woven fabric strips made of a light-weight spunbonded non-woven fabric having a weight per area unit between 10 g/m² and 30 g/m², preferably more than 10 g/m² and less than 20 g/m², are advantageous. For example, a spunbonded non-woven fabric made of polypropylene, having a great tear resistance, is suitable.

Alternatively, carded fiber non-woven fabrics made of polypropylene, polyethylene, polyamide, or polyethylene terephthalate can also be used. The edge regions, in which the non-woven fabric strips overlap the non-woven fabric layer of the laminate strips, can have a width of 2 to 7 mm, preferably more than 4 and less than 5 mm. It is practical if the non-woven fabric strips are firmly connected with the non-woven fabric layer of the laminate strips, for example by means of adhesive or by means of connecting them by means of ultrasound bonding. When adhesive is used, in a preferred embodiment of the invention, the non-woven fabric strips and the non-woven fabric layer of the laminate strips are not glued to one another in the edge regions, proceeding from the edge of the non-woven fabric strip, over a width of maximally 5 mm, preferably over a width between 1 and 4 mm. In the case of an alternative use of an ultrasound method, the connection preferably extends up to the edge of the non-woven fabric strip, thereby increasing the tear resistance of the connection.

In the method according to the invention, laminate strips that are spaced apart and run parallel, consisting of a film strip of an elastic film and a non-woven fabric layer, in each instance, are glued to a planar non-woven fabric layer at their film side. Non-woven fabric strips are applied to the planar non-woven fabric layer between the laminate strips, and the non-woven fabric strips overlap the non-woven fabric layer of the laminate strips in an edge region of the laminate strips.

In a preferred embodiment of the method according to the invention, a laminate of an elastic film, preferably an elastic, extruded mono-film made of a thermoplastic elastomer, and a non-woven fabric layer is drawn off from a roll and cut into laminate strips. It is practical if the film and the non-woven of the laminate are connected by means of adhesive applied in strips, with the strips of adhesive extending in the longitudinal direction of the laminate strips. In a preferred embodiment, an adhesive, for example a hot-melt glue, is applied to the non-woven fabric layer in the form of strips, in the regions in which the laminate strips are laminated on. The adhesive is preferably also applied to the regions between the laminated strips over the entire area. However, the invention is not limited to a connection by means of adhesive. Thus, the connection can also be produced in an ultrasound bonding unit or by other means.

The non-woven fabric strips, in turn, are preferably also provided with an adhesive, for example a hot-melt glue, that is applied, for example, in the form of two strips on the side of the non-woven fabric strips that is laminated onto the non-woven fabric layer and the edge regions of the laminate strips. The laminate strips and the non-woven fabric strips are applied to the non-woven fabric layer in such a manner that they overlap in an edge region having a width between 2 and 7 mm, preferably more than 4 mm and less than 5 mm. If the adhesive is applied to the non-woven fabric layers at a distance of maximally 5 mm, preferably between 1 and 4 mm relative to the edge of the non-woven fabric strips, it can be prevented that adhesive exits at the surface of the laminate material web during the lamination process. If, alternatively, the non-woven fabric strips are connected with the non-woven fabric layer by means of an ultrasound bonding station, the connection preferably extends all the way to the edge of the non-woven fabric strips. If the non-woven fabric strips are connected with the laminate strips and the planar non-woven fabric layer without the use of adhesive, by means of an ultrasound bonding station, contamination of the subsequent rollers will not occur in the case of a tear or a loss of the non-woven fabric strips during the production process.

In order to improve the elastic properties of the laminate material web, or to adapt it to certain requirements, the laminate material web can be over-stretched crosswise to the orientation of the laminate strips after lamination, preferably in a stretching roller arrangement.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
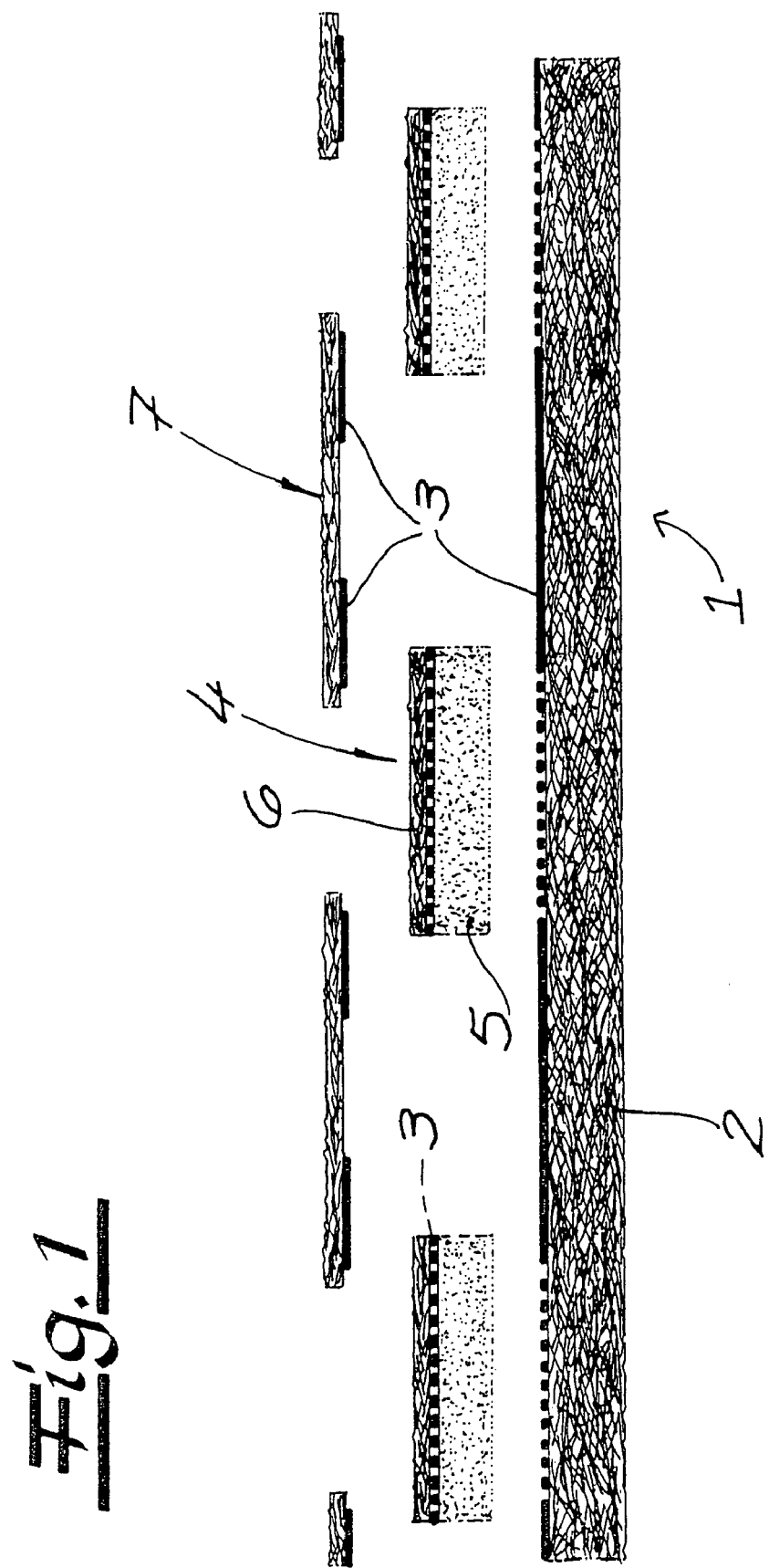
FIG. 1 shows a cross-sectional view of the components of a laminate material web.

Referring now in detail to the drawings, the components of the laminate material web 1 are shown in FIG. 1. An adhesive 3 is applied to a planar non-woven fabric layer 2, which is applied in the form of straight-line or wave-shaped strips of adhesive, which run along the direction of laminate strips 4, in those regions in which laminate strips 4 are laminated on. Between the regions in which laminate strips 4 are laminated on, adhesive 3 is applied to the non-woven fabric layer 2 over its entire area. Each of the laminate strips 4 consists of a film strip 5 of a mono-film of a thermoplastic elastomer, and a non-woven fabric layer 6 of an elastic spunbonded non-woven fabric on the basis of core/mantle multi-filaments. The layers of the laminate strip 4 are connected by means of strips of adhesive that run along the longitudinal direction of the laminate strips 4. The film strips 5 of a mono-film of a thermoplastic elastomer may be a polymer from the group of styrene-butadiene-styrene copolymers (SBS), styrene-isoprene-styrene block copolymers (SIS), styrene-ethene/butene-styrene copolymers (SEBS), elastic polyethylene copolymers, elastic polypropylene copolymers, elastic polyurethane copolymers, elastic polyamide copolymers, or a mixture of these polymers. Other materials could also be envisioned. An adhesive 3, preferably a hot-melt glue, is applied to the non-woven fabric strip 7 of a spunbonded non-woven fabric, on the underside, in the form of two strips, whereby these strips have a maximum distance of 5 mm, preferably from 1 to 4 mm, from the edge of the non-woven fabric strip 7, in each instance.

Figure 2:
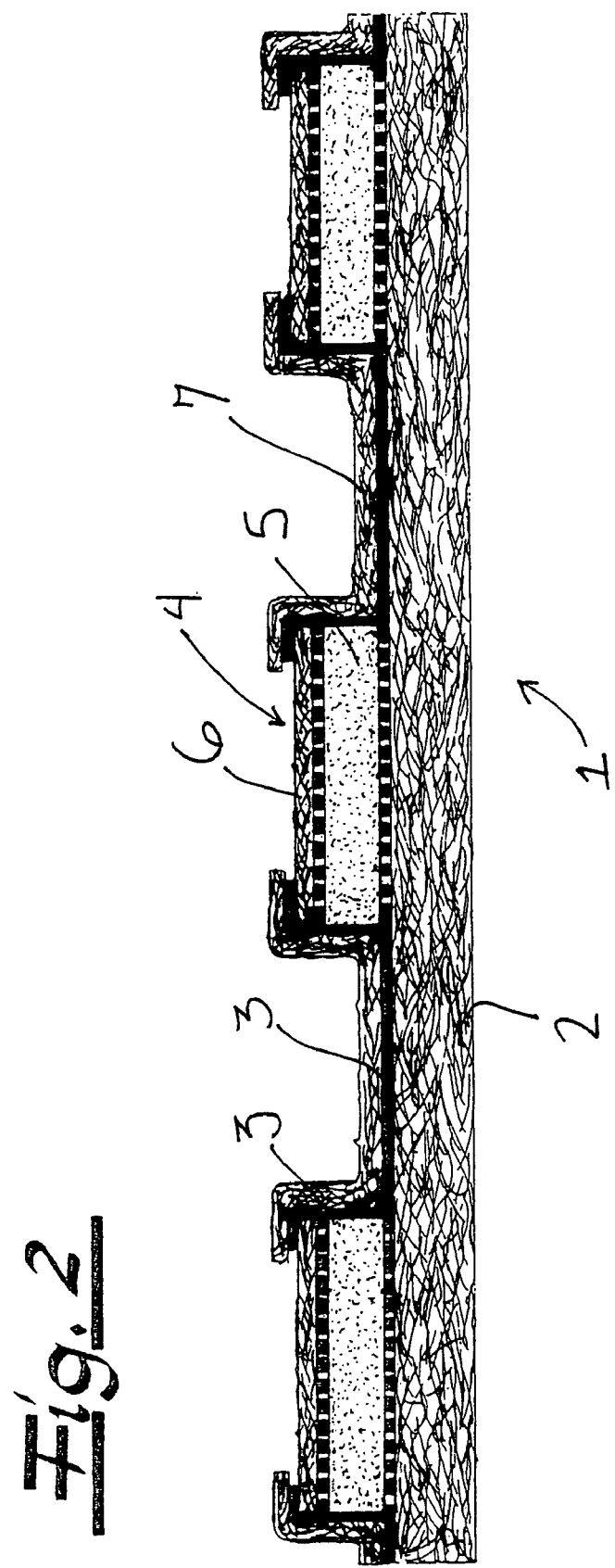
FIG. 2 shows a cross-sectional view of a laminate material web.

FIG. 2 shows a laminate material web 1 that is produced from the components shown in FIG. 1. The edge regions, in which the non-woven fabric strips 7 overlap the non-woven fabric layer 6 of the laminate strips 4, have a width of 2 to 7 mm, for example. Proceeding from the edges of the non-woven fabric strips 7, the non-woven fabric strips 7 are not glued to the non-woven fabric layer 6 of the laminate strips 4 that lies underneath them, over a width of maximally 5 mm. In the regions of the laminate strips 4, the laminate material web 1 is elastic, crosswise to the longitudinal direction of the laminate strips 4. Between the laminate strips 4, where the non-woven fabric strips 7 are glued to the planar non-woven fabric layer 2 over the entire area, the laminate material web 1 is non-elastic.

Figure 3:
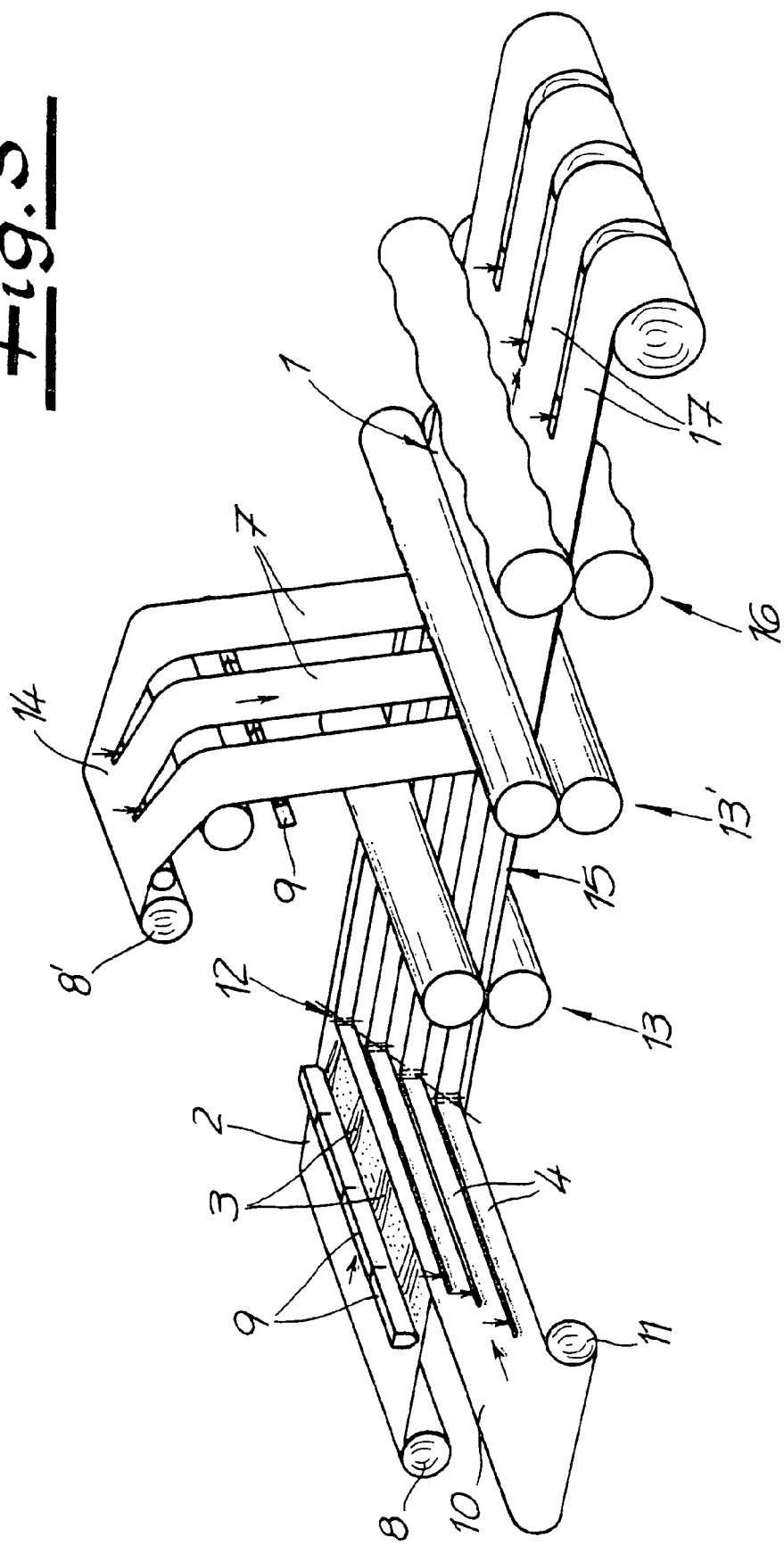
FIG. 3 shows a schematic of the method according to the invention.

The method according to the invention, for the production of a laminate material web 1, is shown schematically in FIG. 3. The non-woven fabric layer 2 is rolled off a non-woven fabric roll 8 and provided with adhesive 3. Adhesive 3 is applied in strips in the regions in which laminate strips 4 are laminated on, and over the entire area in the regions between the laminate strips 4, by means of adhesive nozzles 9. A laminate 10 of an elastically extruded mono-film of a thermoplastic elastomer and a non-woven fabric layer 6 is drawn off from a laminate roll 11 and cut into laminate strips 4. Laminate strips 4 are passed to the non-woven fabric layer 2, which has been provided with adhesive, at a distance from one another and parallel to one another, by a deflection device 12, and connected with this layer in a lamination unit 13. Non-woven fabric 14 is drawn off from a non-woven fabric roll 8' and cut into non-woven fabric strips 7, each of which is provided with two strips of hot-melt glue, using glue nozzles 9, whereby adhesive 3 is applied at a distance of maximally 5 mm from the edge of non-woven fabric strips 7. Non-woven fabric strips 7 are passed to material web 15 and applied to the non-woven fabric layer 2 in such a manner that they overlap non-woven fabric layer 6 of laminate strips 4 in the edge regions of the laminate strips, at a width between 2 and 7 mm. After having passed through another lamination unit 13', laminate material web 1 is passed to a stretching roller arrangement 16, in which it is over-stretched crosswise to its running direction. Laminate material web 1 is subsequently cut into laminate material strips 17 in its longitudinal direction, and rolled up. Sections of these laminate material strips 17 can be used, for example, as an elastic end region or as closure strips of hygiene products, such as disposable diapers.

Figure 4:
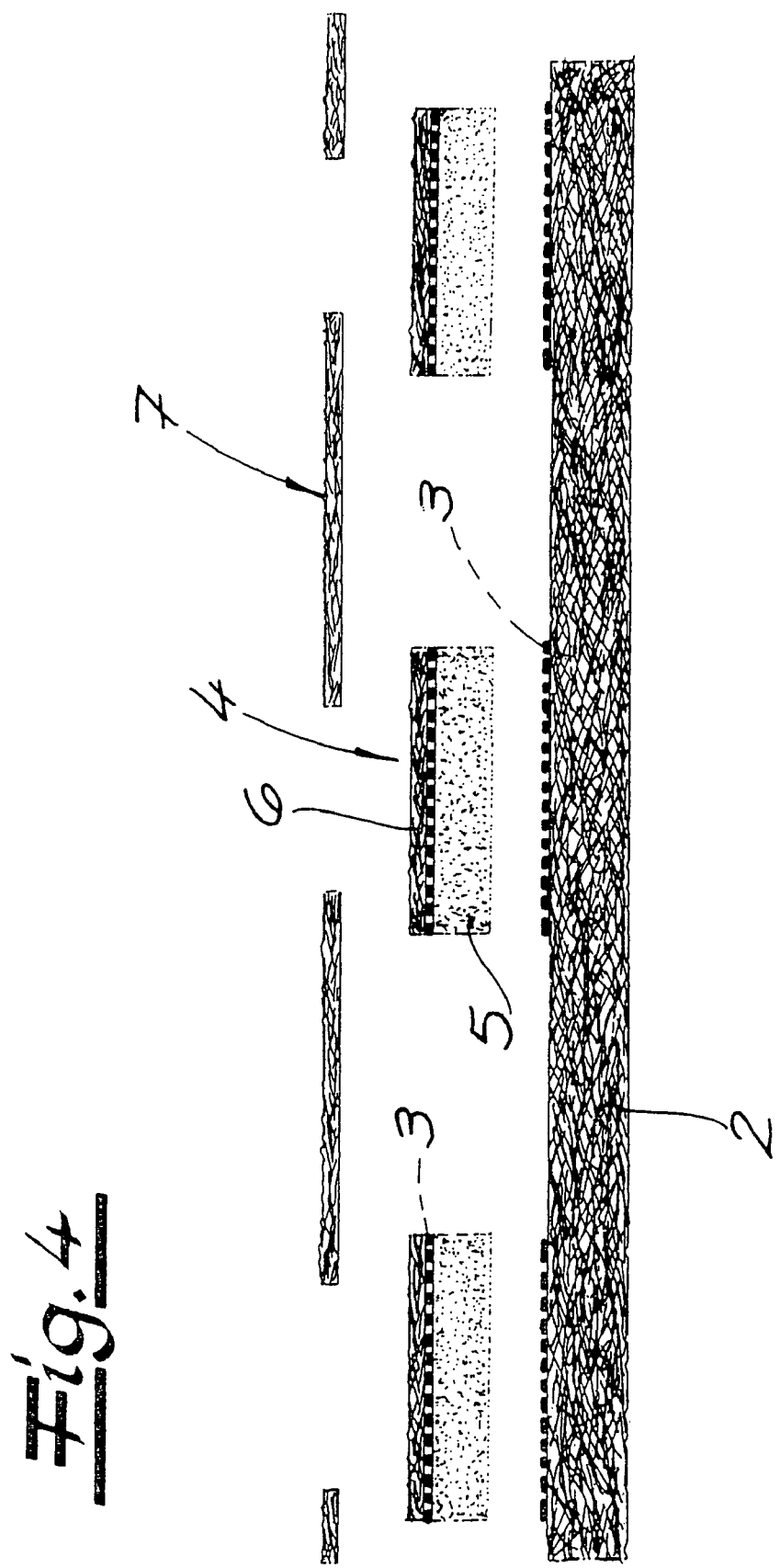
FIG. 4 shows an alternative embodiment of the components of the laminate material web in a cross-sectional representation.

FIG. 4 shows an alternative embodiment of laminate material web 1, whereby non-woven fabric strips 7 are connected with non-woven fabric layer 6 of laminate strips 4 and with planar non-woven fabric layer 2 by means of ultrasound bonding. Adhesive 3 is applied to planar non-woven fabric layer 2 only in the region of laminate strips 4. Because no adhesive 3 is present in the region between laminate strips 4, the risk of contamination of the various machine parts is precluded, to a great extent. In the method for producing laminate material web 1, the non-woven fabric strips 7 are passed to material web 15 and connected with the non-woven fabric layer 6 of laminate strips 4 and with the planar non-woven fabric layer 2 in an ultrasound bonding station.

Accordingly, while only a few embodiments of the present invention have been shown and described, it is obvious that many changes and modifications may be made thereunto without departing from the spirit and scope of the invention.

What is claimed is:

1. A method for the production of a laminate material web having elastic and non-elastic regions, the method comprising the following steps:
    forming laminate strips by connecting a non-woven fabric layer to strips of an elastic film;
    gluing said film strips of said laminate strips to a planar non-woven fabric layer; and
    applying non-woven fabric strips to the planar non-woven fabric layer between the laminate strips, wherein the non-woven fabric strips run parallel to the laminate strips and overlap the non-woven fabric layer of the laminate strips in an edge region of the laminate strips.

2. Method according to claim 1, wherein the laminate strips are formed by drawing off from a roll a laminate of an elastic, extruded mono-film made of a thermoplastic elastomer connected to a non-woven fabric layer, and cutting said laminate into laminate strips.

3. A method according to claim 1, wherein the film strip and the non-woven fabric layer of each laminate strip are connected by strips of adhesive that run in a longitudinal direction of the laminate strips.

4. A method according to claim 1, wherein strips of adhesive are applied in a region in which the laminate strips are laminated, said strips of adhesive running parallel to the laminate strips and over a full area of the planar non-woven fabric layer between the laminate strips.

5. A method according to claim 1, wherein adhesive is applied to the planar non-woven fabric layer over its full area in a region between the laminate strips.

6. A method according to claim 1, wherein the non-woven fabric strips overlap the non-woven fabric layer of the laminate strips in edge regions of the laminate strips with a width of between 2 and 7 mm.

7. A method according to claim 1, wherein adhesive is applied to each of the non-woven fabric strips in the form of two strips of adhesive on each fabric strip.

8. A method according to claim 7, wherein adhesive is applied to the non-woven fabric strips at a distance of at most 5 mm from an edge of the non-woven fabric strips.

9. A method according to claim 1, wherein the non-woven fabric strips are connected with the non-woven fabric layer of the laminate strips by ultrasound bonding in edge regions of the laminate strips.

10. A method according to claim 1, wherein the laminate material web is over-stretched crosswise to an orientation of the laminate strips.

* * * * *